United States Patent [19]

Welstead, Jr. et al.

[11] 3,941,806
[45] Mar. 2, 1976

[54] 7-(α-ACETYLBENZYL)INDOLINE

[75] Inventors: **William John Welstead, Jr.;
Ying-Ho Chen,** both of Richmond, Va.

[73] Assignee: A. H. Robins Company, Richmond, Va.

[22] Filed: Jan. 18, 1972

[21] Appl. No.: 218,833

Related U.S. Application Data

[63] Continuation-in-part of Ser. No. 28,561, April 14, 1970, abandoned.

[52] U.S. Cl. 260/326.11 R; 260/313.1; 260/326.5 R; 424/274
[51] Int. Cl.² ............... C07D 209/12; A61K 31/40
[58] Field of Search .................... 260/326.11

[56] References Cited
UNITED STATES PATENTS
3,579,503   5/1971   Hester .................. 260/239.3
3,679,701   7/1972   Hester .................. 260/326.11

*Primary Examiner*—Nicholas S. Rizzo
*Assistant Examiner*—Diana G. Rivers
*Attorney, Agent, or Firm*—Gordon W. Hueschen

[57] ABSTRACT

The preparation of compounds of the formula

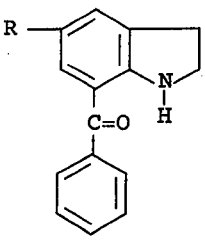

wherein R is selected from the group consisting of hydrogen and chlorine is described. The compounds are useful as chemical intermediates and as anti-inflammatory agents.

1 Claim, No Drawings

7-(α-ACETYLBENZYL)INDOLINE

The present application is a continuation-in-part of our copending application Ser. No. 28,561, filed Apr. 14, 1970, now abandoned.

The present invention relates to heterocyclic organic compounds which may be referred to as benzoylindolines and is more particularly concerned with 5-substituted-7-benzoylindolines, compositions thereof, and processes for making and using the same.

The novel 5-substituted-7-benzoylindolines of the present invention have the formula:

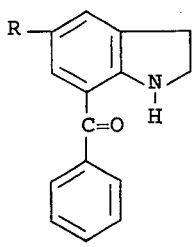

Formula I wherein R is selected from the group consisting of hydrogen and chlorine.

The novel compounds of Formula I have utility as intermediates in the preparation of the compounds disclosed in our copending application Ser. No. 28,561, filed Apr. 14, 1970, and as anti-inflammatory agents.

The compound of Example 1 of the present invention at 316 mg/kg. (per os) reduced the response to pleural irritation. The anti-inflammatory action was demonstrated using a modification of the Evans Blue-Carrageenan Pleural Effusion Test [Sancilio, L. F., Journal of Pharmacology and Experimental Therapeutics 168, 199–204 (1969)]. The potency was determined relative to phenylbutazone, the standard anti-inflammatory agent, and was shown to have twice the anti-inflammatory activity of phenylbutazone.

It is, therefore, an object of the present invention to provide new and useful 5-substituted-7-benzoylindolines. A further object is to provide methods for making the novel compounds of the present invention. Other objects will be apparent to one skilled in the art, and still others will become apparent hereinafter.

The novel compounds of the present invention are prepared by:

a. reacting an indoline-7-carboxylic acid of Formula II

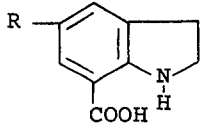

Formula II with phenyllithium wherein R is as defined above;

b. acid hydrolysis of a 1,2-dihydro-4-methyl-5-phenyl-pyrrolo[3,2,1-hi]indole of Formula III

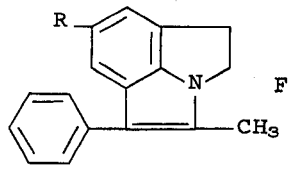

Formula III wherein R is as defined above to give a 7-(α-acetylbenzyl) indoline of Formula IV

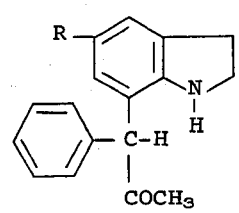

Formula IV which is autoxidized to the 7-benzoylindoline; and c. ozonization of a 1,2-dihydro-4-methyl-5-phenylpyrrolo [3,2,1-hi]indole of Formula III above.

When 5-chloroindoline is used as a starting material, it is possible to introduce a benzoyl group into the 7-position after the nitrogen atom has been protected by acetylation. The acetyl group is then removed by acid hydrolysis.

The starting materials used in preparing the novel compounds of the present invention are prepared by the reaction sequences shown in Chart I.

CHART I

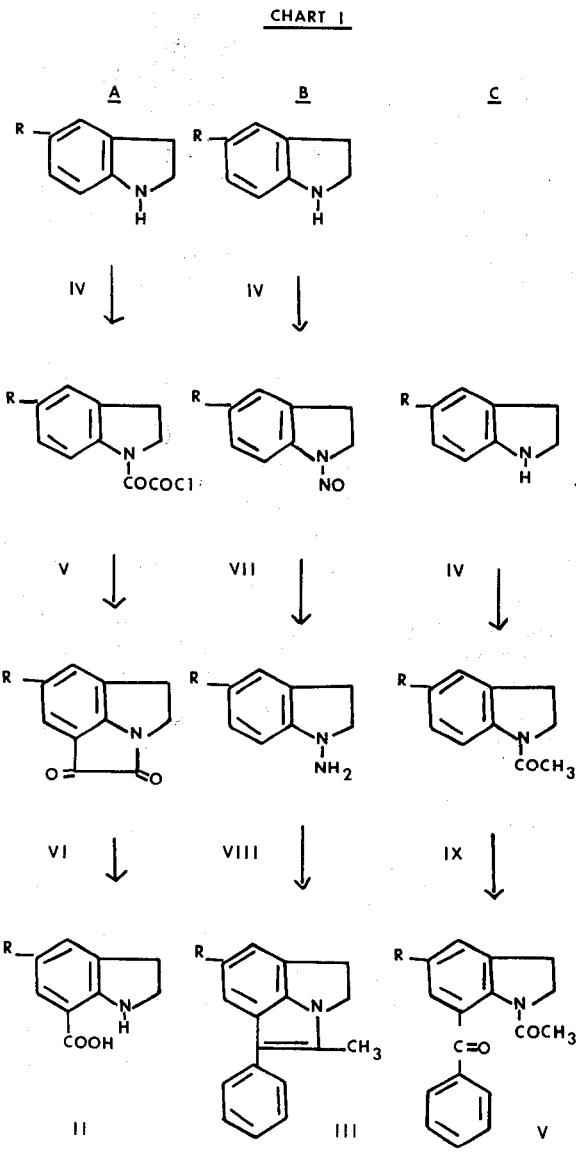

PREPARATION OF STARTING MATERIALS

The starting materials represented by Formulae II, III and V in Chart I can be prepared as shown by procedures A, B, and C. In the preferred method using procedure A, an indoline of Formula IV is dissolved in a chlorinated hydrocarbon solvent, illustratively chloroform, and the solution is added to a solution of oxalyl chloride in the selected solvent at or near room temperature. Subsequent to the addition, the reaction mixture is refluxed for a short period of time of from about one-half to about three hours and is then concentrated at reduced pressure to give the oxalyl chloride compound of Formula V. The oxalyl chloride compound is mixed with aluminum chloride and the mixture stirred until the reactants are thoroughly mixed. The resulting mixture is heated rapidly by external means to a temperature of from about 100°C. to about 125°C. and stirring is continued until the evolution of hydrogen chloride ceases. The crude reaction mixture is hydrolyzed with ice water, the product extracted with a suitable solvent as, for example, chloroform, and the chloroform extracts concentrated to give the dione compound of Formula VI. Although the cyclization to the dione compound is usually carried out as indicated, spontaneous cyclization of the oxalyl chloride compound to the dione may occur.

The dione compound of Formula VI is added to a basic aqueous solution and after stirring for a period of time to dissolve the compound, the dione is oxidized using hydrogen peroxide. The oxidized mixture is stirred until the reaction has been completed, the insoluble materials are extracted with benzene and the basic aqueous solution is carefully neutralized with three normal hydrochloric acid. The neutral solution is extracted with a suitable solvent, illustratively chloroform, the chloroform extracts combined and dried and concentrated to an oil to give the indoline-7-carboxylic acid of Formula II.

The alternate methods of preparing the starting materials are shown by procedures B and C and are more fully illustrated hereinafter in the preparations.

PREPARATION 1

1-Indolineoxalyl Chloride

A stirred solution of 2 moles (254 g.) of oxalyl chloride in 200 ml. of chloroform was treated dropwise with a solution of 1.0 mole (120 g.) of indoline in 200 ml. of chloroform. The stirred mixture was refluxed for 0.5 hours and then concentrated at reduced pressure. The resulting oil (190 g.) was triturated with ether and the solid material which precipitated was filtered off. The filtrate was concentrated to give 120 g. (57%) of 1-indolineoxalyl chloride.

PREPARATION 2

4,5-Dihydropyrrolo[3,2,1-hi]indoline-1,2-dione

A mixture of 90 g. (0.43 mole) of 1-indolineoxalyl chloride and 285 g. (2.1 moles) of aluminum chloride was stirred together in a 3-liter beaker until completely mixed. The mixture was then heated rapidly on a hot plate to 100°–110°C. Stirring was continued for 15 minutes until evolution of hydrogen chloride ceased. The mixture was cooled, hydrolyzed with ice water and extracted with chloroform. The chloroform extract was dried over magnesium sulfate and concentrated to an oil. Trituration with acetone gave 38 g. of a solid mixture which contained about 60% of the desired product. A sample was recrystallized from benzene several times; the recrystallized material melted at 206°–208°C.

Analysis: Calculated for $C_{10}H_7NO_2$: C,69.36; H,4.07; N,8.09. Found: C,69.44; H,4.10; N,8.12

PREPARATION 3

Indoline-7-carboxylic Acid

A crude mixture containing approximately 60% of 4,5-dehydropyrrolo[3,2,1-hi]indoline-1,2-dione was added to a solution of 41 g. of sodium hydroxide in 300 ml. of water. After stirring 30 minutes the mixture was filtered to remove the insolubles, then treated with 46 ml. of 30% hydrogen peroxide and 400 ml. of water. The mixture was stirred 30 minutes, extracted with benzene, then neutralized to pH 7 with 3N hydrochloride acid. The product was extracted into chloroform, the solution dried and concentrated to an oil. The oil crystallized on standing and was recrystallized from acetone-water (Yield 212.8 g.; m.p. 164°–168°C.). A sample recrystallized from acetone melted at 167°–169°C.

Analysis: Calculated for $C_9H_9NO_2$: C, 66.25; H,5.56; N,8.58. Found: C,66.04; H,5.64; N,8.53

PREPARATION 4

5-Chloro-1-nitrosoindoline

A mixture of 77 g. (0.5 mole) of 5-chloroindoline, 80 ml. of concentrated hydrochloride acid and 500 ml. of crushed ice was stirred while a solution of 35 g. of sodium nitrite in 100 ml. of water was added over five minutes. The temperature was kept between 10°C. to 15°C. by addition of ice. The mixture was stirred for 1 hour and then filtered. Recrystallization of the product from benzene-isooctane gave 57 g. (68%) of product which melted at 120°–122°C.

Analysis: Calculated for $C_8H_7ClN_2O$: C,52.61; H,3.86; N,15.34. Found: C,52.83; H,3.86; N,15.28

PREPARATION 5

1-Amino-5-chloroindoline

To a stirred mixture of 50 g. (0.27 mole) of 5-chloro-1-nitrosoindoline, 80 g. (1.2 mole) of zinc and 250 ml. of water was added over a 45 minute period 100 ml. of glacial acetic acid. The mixture was filtered, the filtrate basified with 50% sodium hydroxide solution and the base-insoluble oil extracted with ether. The combined ether extracts were dried, concentrated and the residual oil distilled. 1-Amino-5-chloroindoline was distilled at 96°–98°C./0.1 mm. The oil solidified on standing at room temperature.

PREPARATION 6

7-Chloro-1,2-dihydro-4-methyl-5-phenylpyrrolo[3,2,1-hi]indole.

A mixture of 13 g. (0.077 mole) of 1-amino-5-chloroindoline, 10 g. (0.073 mole) of phenylacetone and 10 g. of sodium acetate in 120 ml. of glacial acetic acid was heated on a steam bath for 1 hour. The mixture was cooled, filtered and the solid material washed with acetic acid and water. The product was recrystallized from benzene-isooctane; yield 12.7 g. (65%); m.p. 202°–204°C.).

Analysis: Calculated for $C_{17}H_{14}ClN$: C,76.25; H,5.27; N,5.23. Found: C,76.10; H,5.36; N,5.19

PREPARATION 7

1-Nitrosoindoline

Indoline (119 g., 1.0 mole) was nitrosated at 10°–15°C. in dilute hydrochloric acid. The 1-nitrosoindoline melted at 83°–85°C. The literature m.p. is 83°C, Chemical Abstracts 54, 19641 (1960).

PREPARATION 8

1-Aminoindoline

1-Aminoindoline was prepared in 67% yield by metal-acid reduction using zinc-acetic acid. The reduced material was purified by distillation, the pure product distilling at 80°C./0.25 mm. The literature b.p. is given as 100°–112°C./12 mm. [Chemical Abstracts, 54, 19641 (1960)].

PREPARATION 9

1,2-Dihydro-4-methyl-5-phenylpyrrolo[3,2,1-hi]indole

A mixture of 50 g. (0.372 mole) of 1-aminoindole, 50 g. (0.372 mole) of phenylacetone, 600 ml. of acetic acid and 50 g. of sodium acetate was heated for one hour on a steam bath. The precipitate which separated from the cooled mixture was collected and washed with isopropyl ether. The product melted at 145°C. The literature m.p. is 145°C., Chemical Abstracts 54, 19641 (1960).

EXAMPLE 1

7-Benzoylindoline

A stirred mixture of 0.165 mole (25 g.) of indoline-7-carboxylic acid and 800 ml. of dry ether was treated dropwise with 0.435 mole of phenyllithium which was prepared from 157 g. (0.435 mole) of bromobenzene, 6.94 g. (0.87 mole) of lithium wire and 500 ml. of dry ether. After addition of the phenyllithium, the reaction mixture was refluxed for three hours and then poured onto ice. After warming to room temperature, the mixture was filtered and the ether layer was separated from the aqueous layer. After washing the ether extract with 1N hydrochloric acid, the product was extracted into 12 N hydrochloric acid. Neutralization of the acidic extract caused precipitation of crude product. The product melted at 119°–122°C.

EXAMPLE 2

7-Benzoyl-5-chloroindoline

A suspension of 5 g. (0.0187 mole) of 7-chloro-1,2-dihydro-4-methyl-5-phenylpyrrolo[3,2,1-hi]indole in 400 ml. of glacial acetic acid was treated with ozone at room temperature until all the suspended material went into solution, the reaction mixture was poured into water and the mixture extracted with chloroform. The chloroform extracts were combined and concentrated to an oil. The oil was treated with a solution of 100 ml. of hydrochloric acid and 100 ml. of glacial acetic acid; the mixture was refluxed four hours and then poured into water. The solution was extracted with chloroform, the solution dried and concentrated to an oil. The oil was dissolved in benzene and chromatographed on 50 g. of magnesium silicate. The material was molecularly distilled to give 1.5 g. (33%) of product. The yellow product melted at 114°–117°C.

Analysis: Calculated for $C_{15}H_{12}ClNO$: C,69.91; H,4.69; N,5.44. Found: C,70.57; H,4.76; N,5.37

EXAMPLE 3

7-Benzoylindoline

Twenty grams (0.086 mole) of 1,2-dihydro-4-methyl-5-phenylpyrrolo[3,2,1-hi]indole in 800 ml. of acetic acid was treated with ozone for 2 hours. The reaction was shown to be completed at the end of 2 hours by thin layer chromatography. The mixture was treated with 300 ml. of concentrated hydrochloric acid and refluxed for 5 hours. The cooled mixture was extracted with ether, the ether extracts washed with 1N sodium hydroxide solution and water. The ether was washed and the residual yellow solid was recrystallized from methanol to give 6.5 g. (34%) of 7-benzoylindoline. The material melted at 121°–122°C.

EXAMPLE 4

7-($\alpha$-Acetylbenzyl)indoline

A mixture of 6.0 g. (0.0258 mole) of 1,2-dihydro-4-methyl-5-phenylpyrrolo[3,2,1-hi]indole in 60 ml. of ethanol, 30 ml. of water and 30 ml. of conc. sulfuric acid was refluxed for one hour. The hot solution was poured into a cold concentrated sodium hydroxide solution and the basic solution was extracted several times with ether. The combined ether extracts were washed with water, dried over sodium sulfate and concentrated at reduced pressure. The residual oil solidified and was recrystallized from petroleum ether to give 7-($\alpha$-acetylbenzyl) indoline which melted at 55°–56°C.

Analysis: Calculated for $C_{17}H_{17}NO$: C,81.24; H,6.82; N,5.37. Found: C,81.27; H,6.89; N,5.59

EXAMPLE 5

7-Benzoylindoline

A toluene solution of crude 7-($\alpha$-acetylbenzoyl)indoline was autoxidized at 80°C. by passing a stream of air through the solution for a period of 3 days. The toluene was removed by evaporation and the residual material transferred to a magnesium silicate column. The 7-benzoylindoline was eluted from the column using benzene. The material melted at 119°–122°C.

EXAMPLE 6

7-Benzoyl-5-chloroindoline

7-Benzoly-5-chloroindoline was prepared by treating 1-acetyl-5-chloroindoline with benzoyl chloride at 120°–175°C. using zinc chloride as a catalyst. The acetyl group was removed by acid hydrolysis to give the yellow colored 7-benzoyl-5-chloroindoline. The yellow solid melted at 112°–115°C. A mixture melting point with material prepared in Example 2 showed no depression.

FORMULATION AND ADMINISTRATION

The present invention also contemplates novel compositions containing the compounds of the invention as active ingredients. In forming the novel compositions of this invention, the active ingredient is incorporated in a suitable carrier, illustratively, a pharmaceutical carrier. Suitable pharmaceutical carriers which are useful in formulating the compositions of this invention include starch, gelatin, glucose, magnesium carbonate, lactose, malt and the like. Liquid compositions are also within the purview of this invention and suitable liquid pharmaceutical carriers include ethyl alcohol, propylene glycol, glycerine, glucose syrup and the like.

Although small quantities of the active materials of the present invention are effective when minor therapy is involved or in cases of administration to subjects having a relatively low body weight, unit dosages are fifty or one hundred milligrams. Fifty to 100 milligrams appear to be optimum per unit dose, while usual broader ranges appear to be 50 to 300 milligrams per unit dose.

The following are examples of compositions formed in accordance with this invention.

1. Capsules

Capsules of 50 mg. of active ingredient per capsule are prepared.

| Typical Blend for Encapsulation | Per Capsule, mg. |
|---|---|
| Active ingredient | 50.0 |
| Lactose | 251.7 |
| Starch | 129.0 |
| Magnesium stearate | 4.3 |
| Total | 435.0 mg. |

Uniformly blend the selected active ingredient with lactose, starch, and magnesium stearate and encapsulate the blend.

2. Tablets

A typical formulation for a tablet containing 50.0 mg. of active ingredient per tablet follows. The formulation may be used for other strengths of active ingredients by adjustment of weight of dicalcium phosphate.

| | | Per Tablet, mg. |
|---|---|---|
| 1. | Active ingredient | 50.0 |
| 2. | Milo starch | 20.0 |
| 3. | Corn starch (paste) | 38.0 |
| 4. | Lactose | 90.0 |
| 5. | Calcium stearate | 2.0 |
| | Total | 200.0 mg. |

Uniformly blend the active ingredient, lactose, milo starch and the corn starch. This blend is granulated using water as a granulating medium. The wet granules are passed through an eight mesh screen and dried at 140° to 160° Fahrenheit overnight. The dried granules are passed through a number ten mesh screen and blended with the proper amount of calcium stearate and this blend is then converted into tablets on a suitable tablet press.

Various modifications and equivalents will be apparent to one skilled in the art and may be made in the compounds, compositions, methods, and procedures of the present invention without departing from the spirit or scope thereof, and it is therefore to be understood that the invention is to be limited only by the scope of the appended claims.

What is claimed is:
1. 7-($\alpha$-Acetylbenzyl)indoline.

* * * * *

UNITED STATES PATENT OFFICE
CERTIFICATE OF CORRECTION

Patent No. 3,941,806   Dated March 2, 1976

Inventor(s) WILLIAM JOHN WELSTEAD, JR.

It is certified that error appears in the above-identified patent and that said Letters Patent are hereby corrected as shown below:

(Col. 5, line 22):   "100° - 112° C." should read:

-- 110° - 112° C. --

Signed and Sealed this

*twenty-ninth* Day of *June 1976*

[SEAL]

Attest:

RUTH C. MASON
*Attesting Officer*

C. MARSHALL DANN
*Commissioner of Patents and Trademarks*